(12) United States Patent
Atzinger et al.

(10) Patent No.: US 7,680,247 B2
(45) Date of Patent: Mar. 16, 2010

(54) COMBINED IMAGE PROCESSING COMPUTER FOR MEDICAL DIAGNOSTICS IN THE FIELDS OF RADIOGRAPHY AND FLUOROSCOPY

(75) Inventors: Franz Atzinger, Nürnberg (DE); Bernhard Geiger, Buckenhof (DE); Heinz Hornegger, Weilersbach (DE); Clemens Joerger, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/860,924

(22) Filed: Sep. 25, 2007

(65) Prior Publication Data

US 2009/0082971 A1 Mar. 26, 2009

(51) Int. Cl.
 *H05G 1/58* (2006.01)
(52) U.S. Cl. ............... 378/116; 378/98.2; 378/190
(58) Field of Classification Search ............ 378/98.2, 378/116, 190
 See application file for complete search history.

(56) References Cited

U.S. PATENT DOCUMENTS

| 1,950,531 | A | * | 3/1934 | Wantz | 378/92 |
|---|---|---|---|---|---|
| 5,022,063 | A | * | 6/1991 | Yokouchi et al. | 378/98.2 |
| 5,117,447 | A | * | 5/1992 | Yokouchi et al. | 378/98.6 |
| 5,636,259 | A | * | 6/1997 | Khutoryansky et al. | 378/197 |
| 6,095,685 | A | * | 8/2000 | Tamura | 378/196 |
| 6,155,713 | A | * | 12/2000 | Watanabe | 378/197 |
| 6,205,347 | B1 | * | 3/2001 | Morgan et al. | 600/407 |
| 6,302,579 | B1 | * | 10/2001 | Meyer et al. | 378/196 |
| 6,318,892 | B1 | * | 11/2001 | Suzuki et al. | 378/197 |
| 6,351,518 | B2 | * | 2/2002 | Yokouchi et al. | 378/98.3 |
| 6,744,912 | B2 | * | 6/2004 | Colbeth et al. | 382/132 |
| 7,220,052 | B2 | * | 5/2007 | Gotoh | 378/193 |

* cited by examiner

*Primary Examiner*—Edward J Glick
*Assistant Examiner*—Thomas R Artman
(74) *Attorney, Agent, or Firm*—Schiff Hardin LLP

(57) ABSTRACT

A combination radiography and fluoroscopy system includes in one embodiment a radiography radiation generator and radiography radiation receiver, a fluoroscopy radiation generator and fluoroscopy radiation receiver, and a single computer system connected to receive signals from the radiography radiation receiver and fluoroscopy radiation receiver. The single computer system includes signal processing paths for the radiography signal and for the fluoroscopy signal wherein some processes or modules are common between the paths and some are path specific. The path specific processes are preferably connected in parallel. Common controls and a common interface are provided to the monitor connected to the computer system. An alternative uses a single radiation receiver for both radiography and fluoroscopy, along with the single computer system. Another alternative provides for separate computers for signal processing of the radiography and fluoroscopy signals, the two computers running substantially identical signal processing programs.

11 Claims, 7 Drawing Sheets

COMBINED IMAGE PROCESSING COMPUTER FOR MEDICAL DIAGNOSTICS IN THE FIELDS OF RADIOGRAPHY AND FLUOROSCOPY

BACKGROUND OF THE INVENTION

1. Field of the Invention

The present invention relates generally to medical imaging and, in particular, to a method and apparatus for combining a radiography system and a fluoroscopy system into a combined medical diagnostic system.

2. Description of the Related Art

Various types of image processing computers (for imaging systems) are used for the two clinical applications of medical diagnostics in fluoroscopy and radiography.

The two imaging systems are characterized by different properties with respect to the frequency and resolution of the generated medical images. In radiography images of unmoving subjects are generated with an optimally high resolution, while in fluoroscopy, images of moving subjects are predominantly generated that have a lower resolution than the images in radiography. In other words, radiography produces high resolution still images whereas fluoroscopy produces lower resolution moving images.

The known prior art provides that different systems are used for the image processing in the different systems for fluoroscopy and radiography. The computers which are used are optimized for the respective requirement of the imaging system. The most important characteristic data for the image computers of the various systems are listed in the following For a Radiography System:

Image size: approximately $3000^2$ (approximately 5-10 megapixels per image)

Image frequency: approximately 2 images per minute (with a maximum of 10 images per minute)

Duration of the image calculation: a maximum of a few seconds

Acceleration voltage of the x-ray tube: approximately 40-150 kV

Dose: 1 μGy to 10 μGy

Image processing algorithms: linear and non-linear, multiscalar frequency filters Fluoroscopy:

Image size: approximately $1000^2$ (approximately 1 megapixel per image)

Image frequency: approximately 0.5 images per second up to a maximum of 30 images per second Duration of the image calculation: a few milliseconds Acceleration voltage of the x-ray tube: approximately 40-90 kV Dose: 3 nGy up to 1 μGy Image processing algorithms: linear frequency filters In addition to the technical data being handled by the two systems, the two different computers also exhibit differences in the operation since the workflows in the image generation are different between fluoroscopy and radiography. The different operating workflows between the two acquisition methods are thereby depicted in different operating interfaces on the computer monitors.

In systems with different detectors for fluoroscopy and radiography, an image chain must be provided for each different detector that can calculate images with the different resolution and frequency. These images are generated either by different radiation receivers for the different applications or may be generated by a combined radiation receiver for both image types.

SUMMARY OF THE INVENTION

The present invention provides an apparatus and method for combining the previously different image processing computers for image generation in fluoroscopy and radiography medical applications into one system with which it is possible to perform fluoroscopy and radiography imaging in a single system for medical diagnostics.

The present method and apparatus provides a combined radiography and fluoroscopy system in which the image data from the respective different sensors is processed on a single image processing computer. An alternative provides a single radiation receiver capable of receiving and generating images from both radiography and fluoroscopy signals. This single receiver is connected to the single image processing computer. A further alternative provides different radiation receivers for the radiography and fluoroscopy devices and different computer systems connected to the different radiation receivers, the different computer systems being substantially identical as between the two systems.

The use of an image chain for both image types can be achieved in that the individual elements of the image chain are designed such that both the different matrix sizes and the different image frequencies can be calculated. If some image chain components do not have the capability of being used for both image types, the corresponding parts must be separately realized for the respective requirements. These parts must then be connected in parallel with corresponding parts for the other image type in the sequence of the calculation steps, and the generated images are directed through the one or the other part of the image chain depending on the image requirements.

DETAILED DESCRIPTION OF THE PREFERRED EMBODIMENTS

Figure 1:
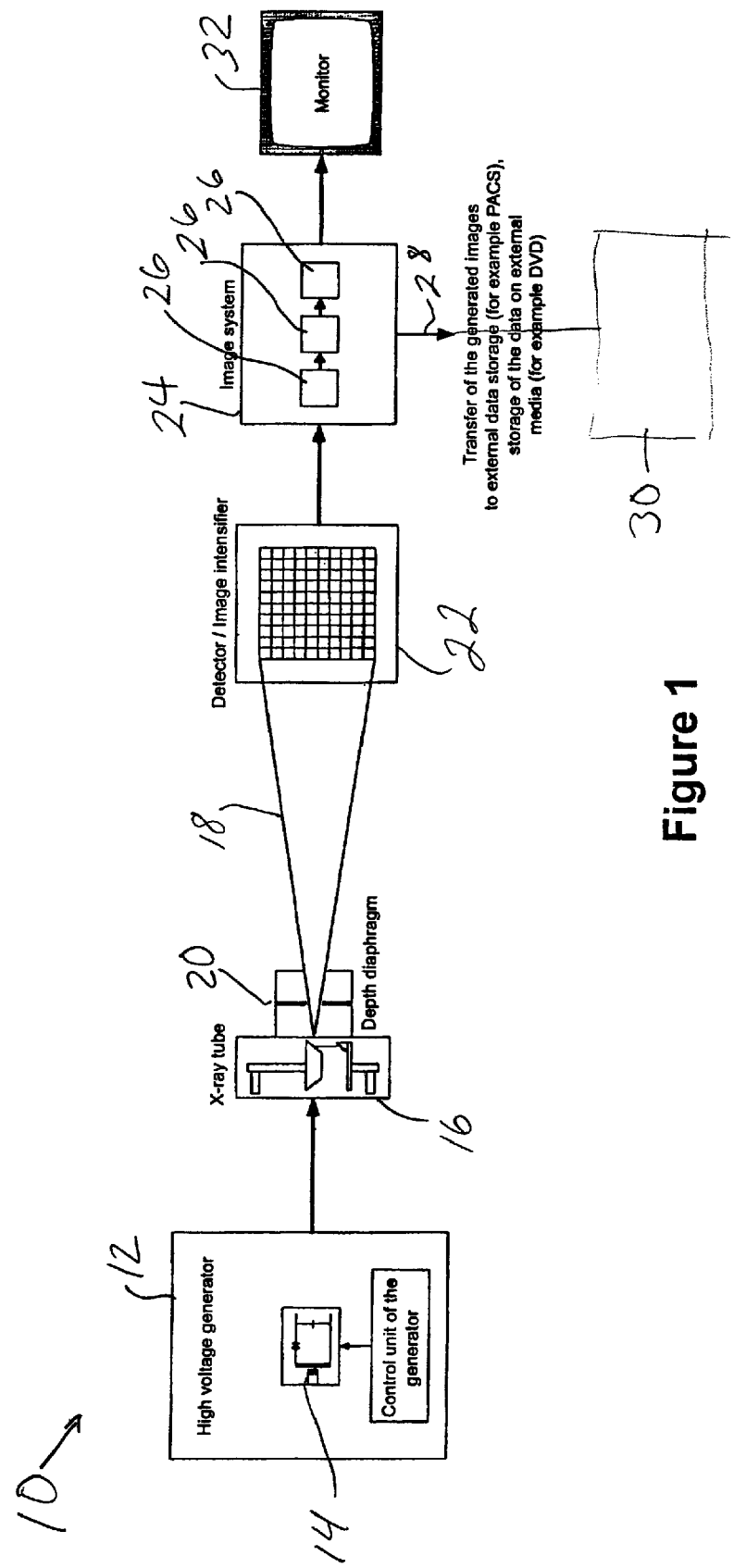
FIG. 1 is a schematic representation of a radiography system, also referred to as an x-ray system, for generating medical images.

In FIG. 1, an imaging system 10 for medical imaging using x-rays includes a high voltage generator 12 that generates the high voltages necessary to power the x-ray generating apparatus. The high voltage generator 12 includes a control unit 14 by which the power is controlled. Power from the high voltage generator 12 is provided to an x-ray tube 16 where it is used to generate x-rays of a predetermined range of wavelengths. The x-ray energy from the x-ray tube 16 is focused into a beam 18 and passes through a diaphragm 20 is used to set the depth of field for the image. The beam 18 is directed toward an object to be imaged, which for a medical imaging system is a patient (not shown) so that portions of the beam are attenuated by the patient's tissues. The resulting patient image is detected by a detector 22 positioned on the opposite side of the patient from the x-ray tube 16. The detector 22 of the preferred embodiment is a digital image detector for x-rays of at least part of the range of wavelengths generated by the x-ray tube 16. The detector 22 also serves as a image intensifier to amplify faint image information.

The radiation detector and image intensifier 22 transmits an image signal to an image system 24. The image system 24 performs various image processing steps on the image data, as is known, to control contrast and exposure in the image, decrease noise in the image, and control object definition in the image, for example. Any known image processing steps may be applied. Image processing functions are performed by image processing units 26 in the image system 24. More or fewer image processing units 26 may be provided as needed. The processed image data is preferably output at 28 as a generated image signal that may be transmitted to a storage system 30. The storage system 30 may be an external storage system using PACS (Picture Archiving and Communication System) technology to store the image on an external media, such as a DVD (Digital Versatile Disc). The storage system 30 may instead include a hard drive based storage, solid state storage, tape storage or other storage system. The generated image is also provided to a monitor 32 so that the image data may be viewed by a medical professional, such as a doctor. The monitor 32 may display the image immediately after processing or after the image has been stored.

Figure 2:
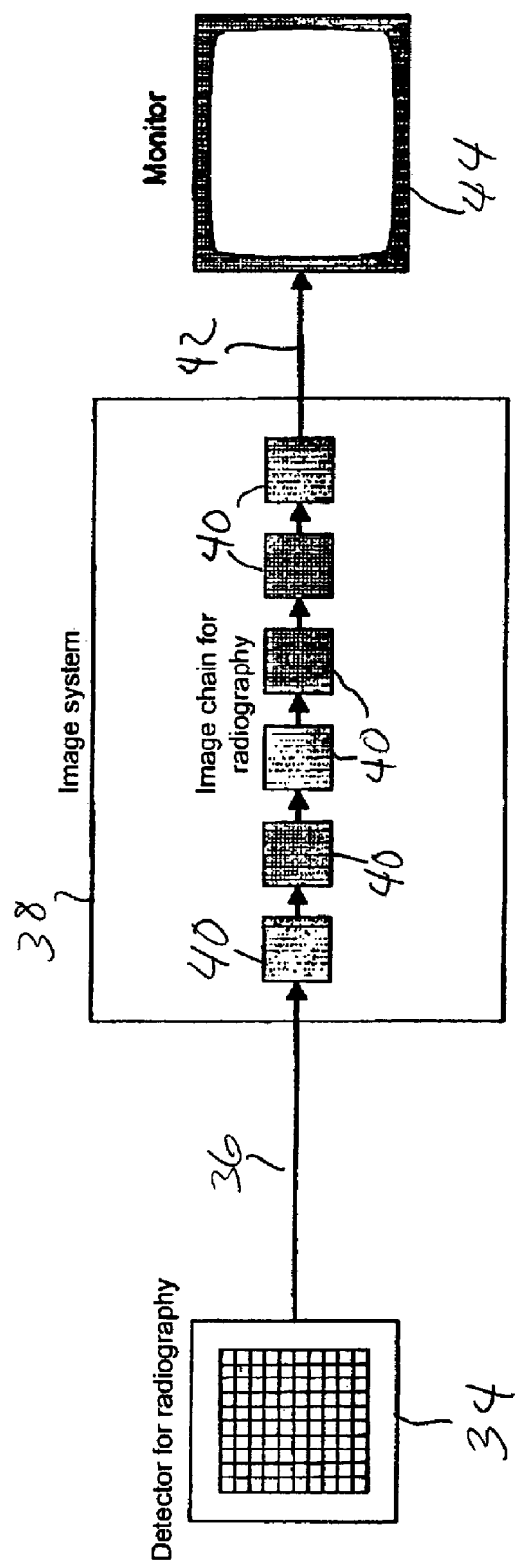
FIG. 2 is a schematic representation of an image system for image data processing of data from a radiography system.

In FIG. 2 an imaging system portion of a radiography system, is shown. The radiography system includes a radiography detector 34 that senses the x-ray beam that has been directed through some portion of the patient and provides a detector signal 36 to an image system 38. The detector 34 has a predetermined resolution which for most radiography systems is a high resolution, and operates at a predetermined frequency range which is the frequency range used for radiography. The image system 38 includes image processing units 40 that perform image processing steps on the detector signal 36 to produce a generated image signal 42 that is provided to a monitor 49. The image processing units 40 are specific to the radiography image signal 36.

Figure 3:
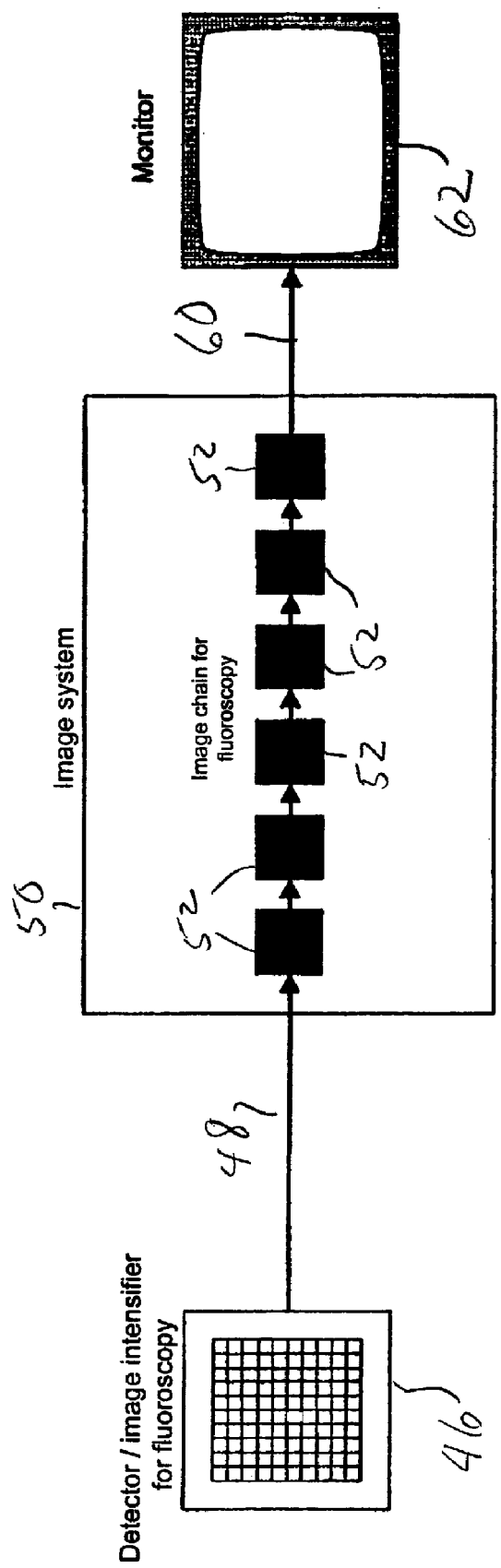
FIG. 3 is a schematic representation of an image system for image data processing of data from a fluoroscopy system.

FIG. 3 shows a comparable portion of an imaging system for fluoroscopy. The system includes a detector and image intensifier 46 for receiving the fluoroscopic energy beam that has been directed through a portion of the patient. The fluoroscopic detector 46 produces a detector signal 48 that is provided to an image system 50. The fluoroscopic detector 46 differs from the radiographic detector 34 in a number of ways, including the wavelength or frequency of the signal to be detected and the resolution of the detector. Like the image system of the radiography device of FIG. 2, the image system 50 of the fluoroscopy system has image processing units 52. However, the image processing units 52 differ from those of the radiography system due to differences in the data and the processing needs of the system. The processing units 52 produce a generated image signal 60 that is forwarded to a monitor 62 for viewing by a medical professional.

Figure 4:
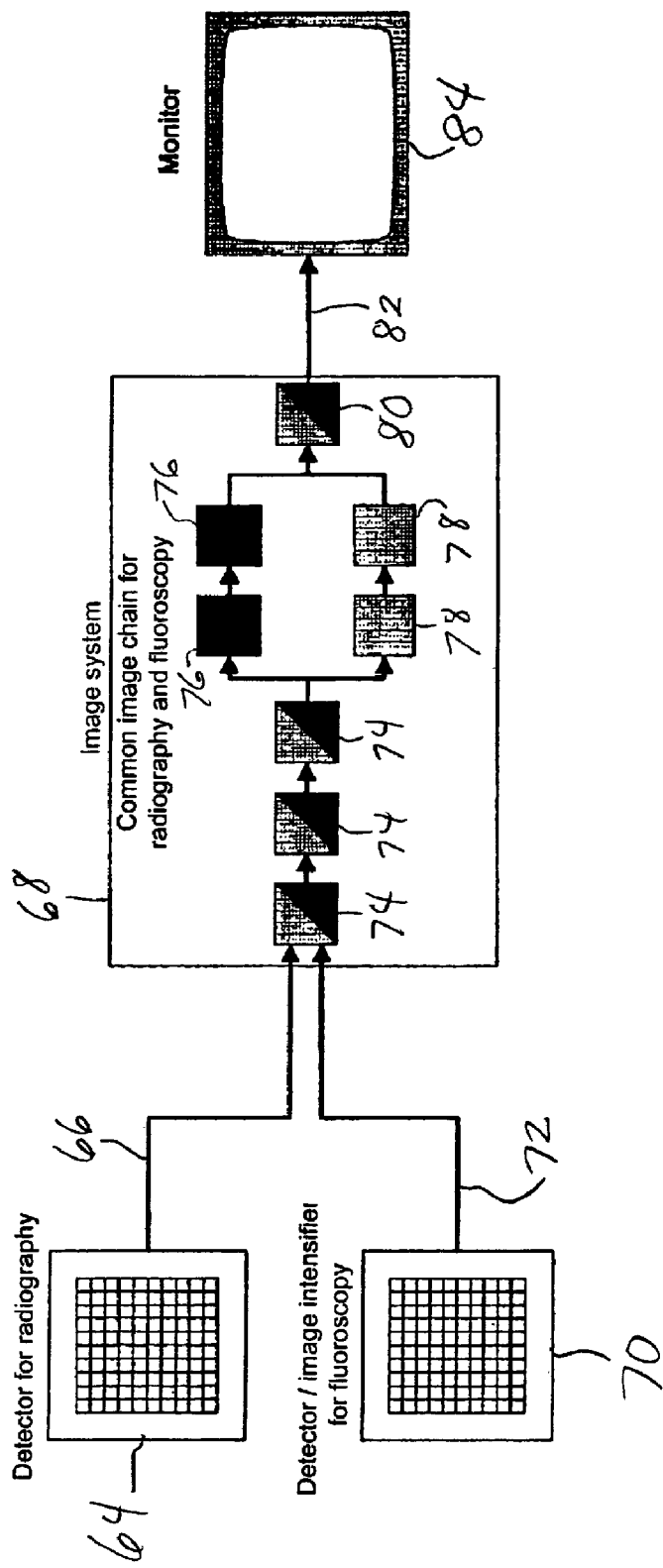
FIG. 4 is a schematic representation of a combined image system for image data processing of data from a radiography imaging device and of data from a fluoroscopy imaging device.

According to one aspect of the invention, a combined system is provided that combines both radiography and fluoroscopy in one system. In FIG. 4, a detector 64 is provided for detecting the radiography beam and transmitting a detected radiography signal 66 to an image system 68. A detector and image intensifier 70 for a fluoroscope beam is also provided. The fluoroscope detector and image intensifier 70 generates a detector signal 72 that is also provided to the same image system 68 as is used for the radiographic signal. The image system 68 uses the same processing units 74 to process both the radiography signal 66 as well as the fluoroscopy signal 72. These processes 74, which are also referred to as modules, are capable of being performed on the both signals regardless of the differences in resolution and frequency. The processes which perform on both signal types are referred to as common processes. For some processes 76, the processing of the two signals is significantly different and so separate processing units 76 and 78 are provided in parallel paths. The processing units 76 perform fluoroscopy specific processes, while the processing units 78 perform radiography specific processes. The processes that are specific to the signal are referred to as path specific processes. The process 76 is path specific to the fluoroscopy signal processing path and the process 78 is path specific to the radiography signal processing path. The respective detector specific process 76 or 78 is completed and the resulting signal sent to a common processing unit 80 performs a further process on the image signal to generate the generated image signal 82. The generated image signal 82 is provided to a monitor 84 for display, although it may also be stored prior to or con with display, as noted above.

The arrangement of detector specific processes and common processes may differ from that shown so that detector specific processes may be provided at the beginning of the processing sequence, at the end, or at any point along the sequence. The signal processing sequence may be split into detector specific process several times in the sequence, or only once. Changes in settings by the user may result in changes in which processes are used and whether the process requires a detector specific process or whether a common process can be used.

The processes in the image processing sequence may be performed by software, hardware, firmware or a combination thereof. The processes may be performed by modules that are distinct from one another or by modules that are integrated with one or more other modules. The needs of various users differ in terms of what they require of a medical image and so different modules or processes may be used depending on a user's needs.

Figure 5:
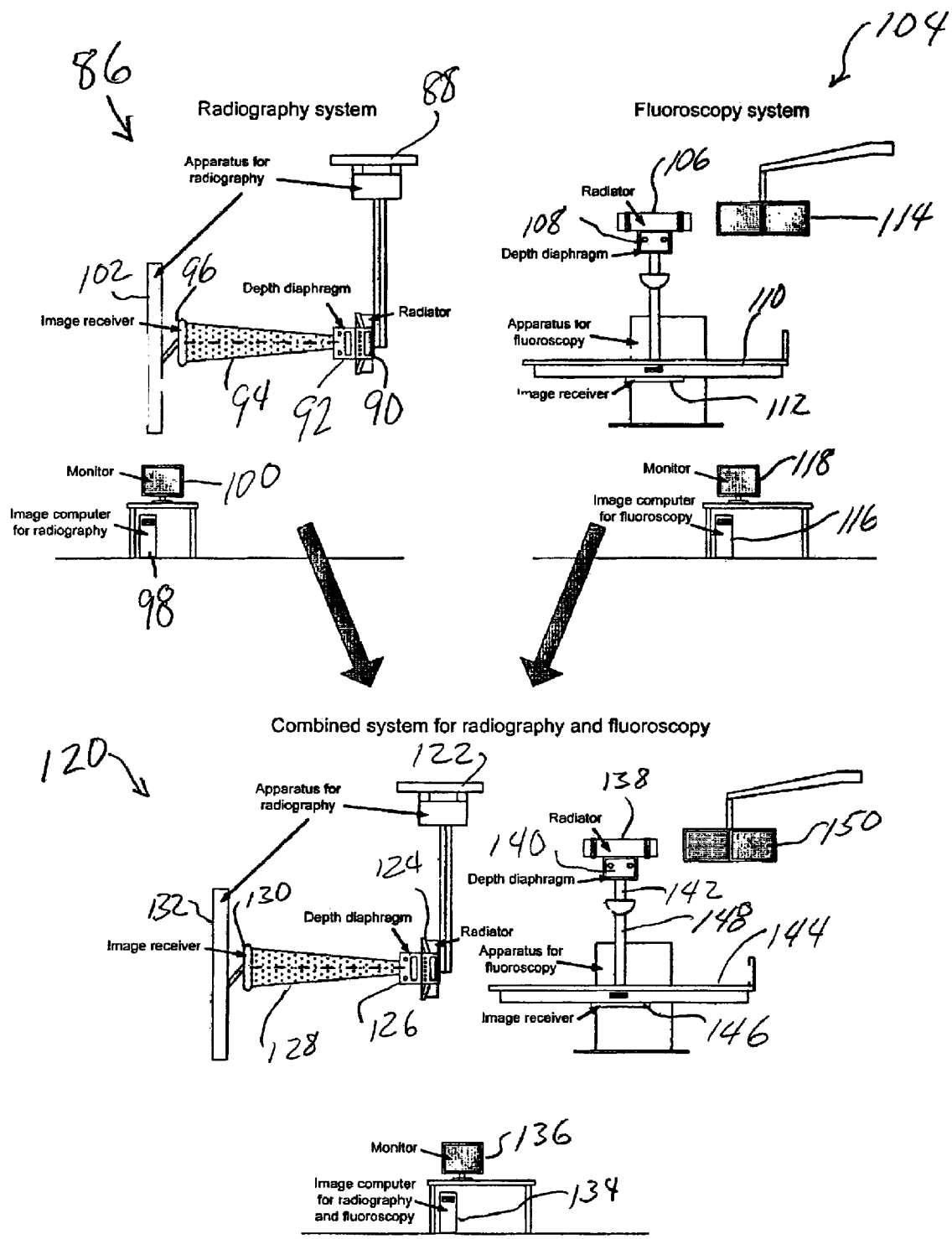
FIG. 5 is a schematic representation of combination of a fluoroscopy system and radiography system into a common system with separate image receivers and a common image computer for processing of both image types.

Referring to FIG. 5, a radiography system 86 typically includes a mount 88 that supports a radiation generator 90 including a depth diaphragm 92 to generate a beam 94 directed toward a patient (not shown), such as for a chest x-ray. The patient is positioned in the beam path and the beam is detected by a radiation receiver 96. The beam generator 90 and radiation receiver 96 are oriented in that example to image a standing patient for a chest x-ray, for example. The radiation receiver 96 is mounted on a wall or wall unit 102. The radiation receiver 96 sends the signal to a computer 98 that performs radiography image processing radiation so that the generated image can be displayed on a monitor 100. Typically, the medical personnel are not in the room during the radiographic imaging.

A fluoroscopy system 104 includes a radiation generator 106 with a depth of field diaphragm 108. The radiation generator 106 directs a beam to a table 110 where a patient who is to receive treatment, such inserting a cardiac stent or a pacemaker lead, for example, is lying. A radiation receiver 112 is mounted below the table 110. A light 114 is positioned above the table 110 for better visibility of the patient by the medical personnel. The fluoroscopic images are typically made during an ongoing procedure on the patient and the medical personnel are in the room with the patient to perform the procedure. The image signal from the image receiver 112 is forwarded to a computer 116 that is connected to a monitor 118 on which the image may be viewed. Since the fluoroscopic image is typically being viewed by the medical personnel during the medical procedure, it is important that the monitor 118 be positioned within easy view of the medical personnel performing the procedure.

According to aspects of the invention, a combined system 120 for radiography and fluoroscopy is provided. The combined system includes a mount 122 supporting a radiation generator 124 for radiographic signals. A depth diaphragm 126 directs a beam 128 to a radiation receiver 130 that is mounted on a wall or wall unit 132. The signal is sent from the receiver 130 to a computer 134 that includes a monitor 136. The combined system 120 also includes a radiation generator 138 that generates fluoroscopic signals which pass through a depth diaphragm 140 to form a beam 142 which is directed to a patient (not shown) on a table 144. A fluoroscopic radiation detector 146 is disposed in or beneath the table 144 to sense the fluoroscopic radiation. A beam shield 148 is provided to shield medical personnel that are nearby from the energy of the beam 142. Lighting 150 is provided for illumination during the medical procedure.

The fluoroscopic signal detected by the detector 146 is transmitted to the same computer 134 for processing as the radiographic signals. The same monitor 136 is used to view the results. The fluoroscopic image data and radiographic image data is processed according to FIG. 4, for example, or the variations discussed in conjunction therewith. Thus, only one computer 134 and monitor 136 need by provided and only one of each of the common modules in the image processing sequence. A savings of hardware and software results. Further, the common image processing system enables a user to learn only one system and still be able to perform processing on both types of signals.

Figure 6:
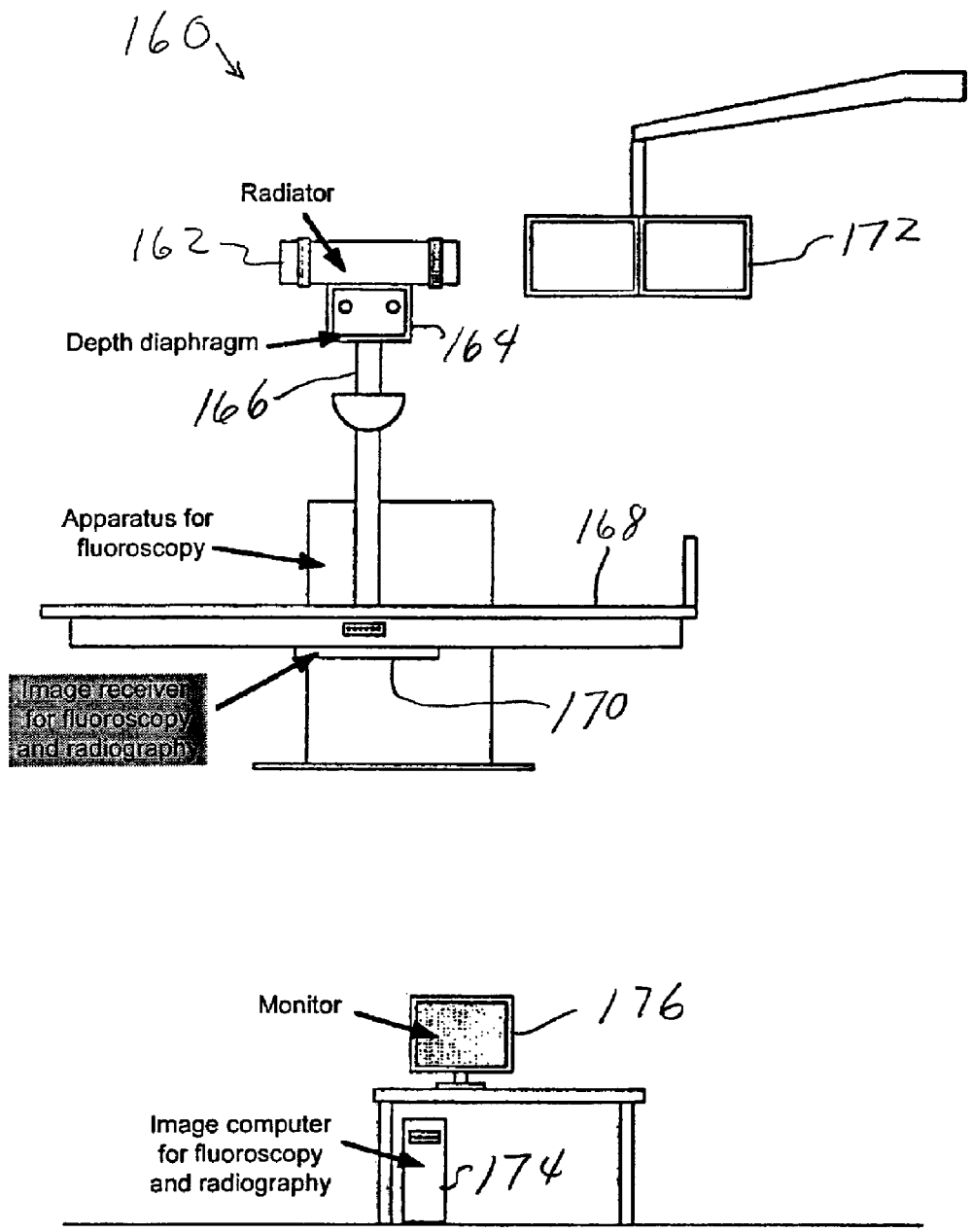
FIG. 6 is a schematic representation of combination of a fluoroscopy and radiography system in a common system with a common radiation receiver and a common image computer for processing of both image types.

Turning to FIG. 6, the combined system 160 of an alternative embodiment includes a single radiation generator 162 or radiator that is powered to generate x-ray radiation. A controller in the radiation generator 162 controls the energy output level and radiation frequency level to either generate radiographic radiation or fluoroscopic radiation. A depth diaphragm 164 is provided to control the depth of field of the image. Since the combined system 160 will be used for both radiographic and fluoroscopic imaging, a beam shield 166 is provided to shield medical personnel from the beam. The shield 166 may be removable as needed, or not. A table 168 on which to place the patient during the procedure is provided, and a combined radiographic and fluoroscopic radiation receiver 170 is provided beneath the table 168 in a position opposite the generator 162 from the patients. A light fixture 172 is provided in the room to improve the view by the medical personnel.

The radiation receiver 170 has a resolution sufficient for high resolution radiographic images but it may be switched to a lower resolution mode for the fluoroscopic imaging process. The read-out rate from the detector 170 may also be switched to enable the rapid read-out required for real time fluoroscopic imaging. The detector 170 of a preferred embodiment has a wide enough frequency range to detect either the radiographic or the fluoroscopic radiation, although it is also possible that the detector may be switched to operate at different frequencies.

The radiation generator and detector of the combined system may be operable at the operating characteristics of the known radiographic and fluoroscopic systems or may operate outside of those parameters, such as at some frequency, energy level or resolution between the known parameters or beyond the known parameters.

The detector signal from the detector 170 is provided to a single computer 174 where processing is performed on the signal to provide a generated image signal. The processing preferably is performed in accordance with FIG. 4 or one of the variations discussed in conjunction therewith. The resulting image signal is displayed on a monitor 176 and/or stored on a storage system.

Figure 7:
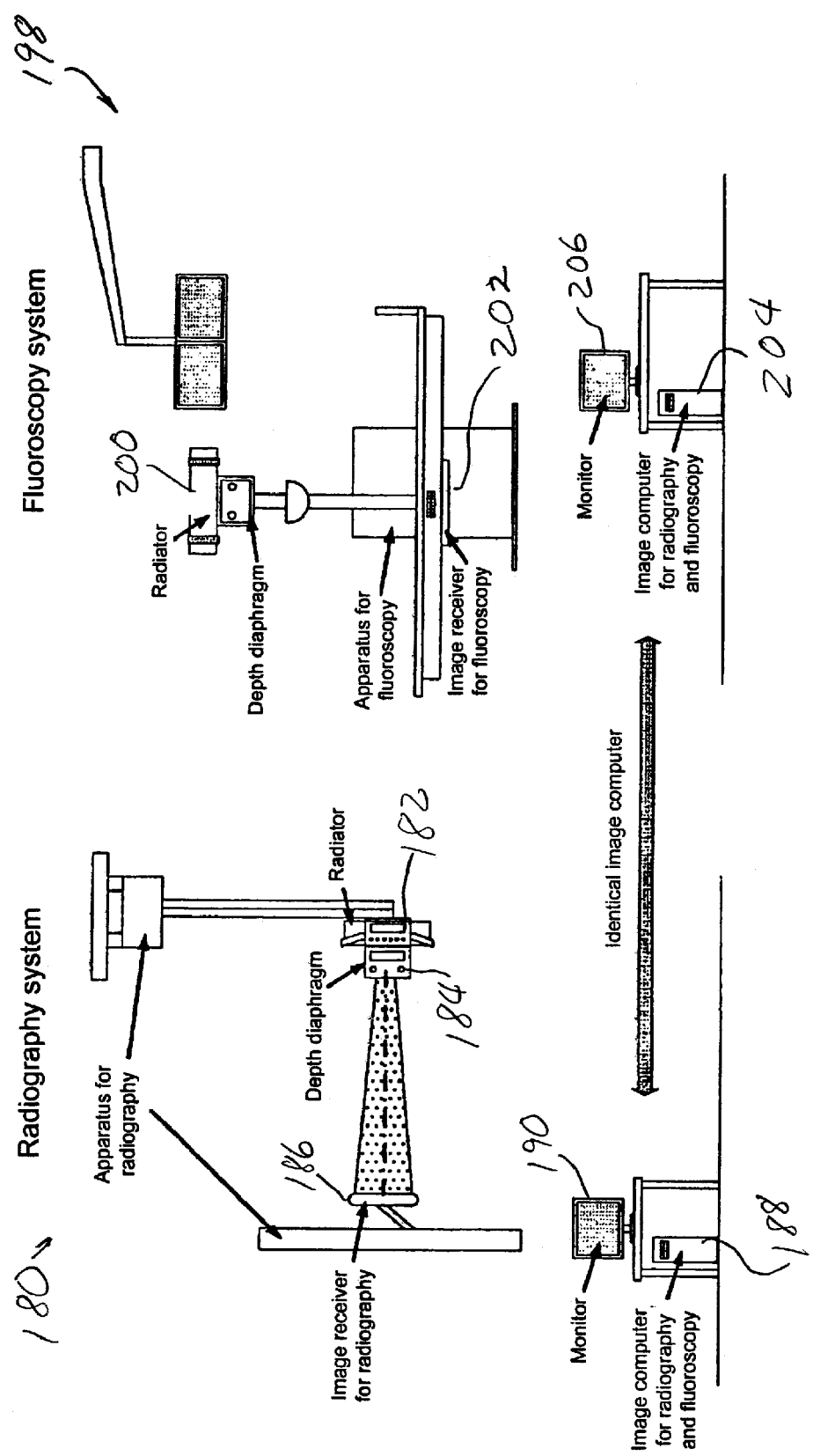
FIG. 7 is a schematic representation of combination of a fluoroscopy and radiography system in a common system with separate image receivers and separate but substantially identical image computers for both image processing tasks.

FIG. 7 shows a further variation of the combined system. A radiographic system 180 is provided, which has a radiation generator 182, depth diaphragm 184, and radiation detector 186 like that described previously. The detector signal is sent to a computer 188 for processing and display on a monitor 190. The computer 188 runs the combined process shown in FIG. 4 so that common processes are handled by common modules and a common interface appears on the monitor.

A fluoroscopic system 198 is also provided having a separate radiation generator 200 and separate radiation detector 202. The signal from the fluoroscopic radiation detector 202 is transmitted to a separate computer 204 for processing and display on a separate monitor 206. The computer 204 performs the combined process as shown in FIG. 4 or as discussed in conjunction therewith. The computers 188 of the radiographic system and 204 of the fluoroscopic system are substantially identical in a preferred embodiment. The hardware portion, at least as to processing the signals, may be substantially identical or may be different as between the computers 188 and 204. More importantly, the software that performs the image processing processes is substantially identical as between the two computers 188 and 204. The same modules are provided for the processing, the same user interface and same user commands are provided and the same output format is provided as between the two computers.

Only one software program is required for the two systems. The user need only learn the commands and interface of one program in order to operate both systems. More importantly, medical personnel who are being asked to base a diagnosis or treatment on the information displayed by the computer need remember only one display type or interface format. Reducing the differences between the information provided from the two imaging systems means less risk of a mistake by a busy doctor and less non-medical information the doctor must learn, enabling the doctor to focus on the patient rather than technology. As such, the present invention makes the technology more transparent, enabling more of the doctor's time to be spent on the patient.

The combined processing units reduce costs in the system and provide other advantages. For example, both the generated images from the dedicated radiation receivers for fluoroscopy and radiography and images from a combined radiation receiver can be calculated with a universal image system.

This means that x-ray systems can be realized with such an image system that can be used for both types of medical diagnostics; these systems can thus be used more universally than systems that support only one type of diagnostics. An expanded application range of a combined x-ray system results with simultaneously relatively slice cost increase relative to a dedicated system.

Moreover, the type diversity of image systems in different x-ray systems is reduced via a universal image system. This simplifies the development and manufacturing process of such systems. It additionally offers the user the advantage of the greater ease of learning with regard to the handling of the systems since essential operating elements at the user interface of the image system are identical for the implementation of the two different medical applications.

Combination of a fluoro- and radiography system in a common system with separate image receivers and a common image computer for both tasks.

Although other modifications and changes may be suggested by those skilled in the art, it is the intention of the inventors to embody within the patent warranted hereon all changes and modifications as reasonably and properly come within the scope of their contribution to the art.

We claim:

1. A combination radiography and fluoroscopy system, comprising:
   a radiation generator operable to generate a beam of radiation, said radiation generator being operable to generate at least one of radiograph radiation and fluoroscopy radiation;
   a radiation receiver disposed in a path of said beam and operable to generate a radiation detector signal from radiation received by said radiation receiver; and
   a computer system connected to receive said radiation detector signal from said radiation receiver, said computer system being operable to process either radiography radiation detector signals or fluoroscopy radiation detector signals, said computer system including a first signal path for processing radiographic radiation detector signals as radiographic image signals and a second signal path for processing fluoroscopic radiation detector signals as fluoroscopic image signals, said first and second signal paths including a plurality of processing modules wherein at least one of said processing modules is common to and shared by both said first and second signal paths, said first signal path including first separate processing modules, and said second signal path including second separate processing modules that are distinct from said first separate processing modules.

2. A combination radiography and fluoroscopy system as claimed in claim 1, wherein said radiation generator is a first radiation generator that is operable to generate a radiography radiation beam, and further comprising:
   a second radiation generator that is operable to generate a fluoroscopy radiation beam.

3. A combination radiography and fluoroscopy system as claimed in claim 2, wherein said radiation receiver is a first radiation receiver that is operable for generating a radiography radiation detector signal from a radiography radiation beam, and further comprising:
   a second radiation receiver disposed in a path of said fluoroscopy radiation beam and operable to generate a fluoroscopy radiation detector signal from said fluoroscopy radiation beam.

4. A combination radiography and fluoroscopy system as claimed in claim 3, wherein said computer system is connected to receive said radiography radiation detector signal from said first radiation receiver and is connected to receive said fluoroscopy radiation detector signal from said second radiation receiver, said computer system including:
   said first signal path for processing said radiography radiation detector signal and
   said second signal path for processing said fluoroscopy radiation detector signal, said first and second signal paths having common processing modules.

5. A combination radiography and fluoroscopy system as claimed in claim 4, wherein said first signal path includes at least one first module for processing only radiography signals, said second signal path includes at least one second module for processing only fluoroscopy signals, said first and second modules being connected in parallel.

6. A combination radiography and fluoroscopy system as claimed in claim 4, wherein said computer system includes a single computer system connected to receive and process said radiography radiation detector signal and said fluoroscopy radiation detector signal.

7. A combination radiography and fluoroscopy system as claimed in claim 4, wherein said computer system includes first and second computer systems connected to respective ones of said first and second radiation receivers, said first and second computer systems operating substantially identical signal processing programs for processing the respective radiography radiation detector signal and fluoroscopy radiation detector signal, said substantially identical signal processing programs including substantially identical modules between the two programs that are operable to process the radiography radiation detector signal in said first computer system and operable to process the fluoroscopy radiation detector signal in said second computer system.

8. A combination radiography and fluoroscopy system, comprising:
   a first radiation generator operable to generate a radiography radiation beam;
   a first radiation receiver disposed in a path of said radiography beam and operable to generate a radiation signal from said radiography radiation beam;
   a second radiation generator that is operable to generate a fluoroscopy radiation beam;
   a second radiation receiver disposed in a path of said fluoroscopy radiation beam and operable to generate a fluoroscopy radiation signal from said fluoroscopy radiation beam;
   a computer system connected to receive said radiography radiation signal from said first radiation receiver and connected to receive said fluoroscopy radiation signal from said second radiation receiver, said computer system including:
      a first signal path for processing said radiography radiation signal to generate a radiography image,
      a second signal path for processing said fluoroscopy radiation signal to generate a fluoroscopy image, said first and second signal paths having common modules that are shared by both said first and second signal paths, said first and second signal paths including path specific modules specific to respective radiography and fluoroscopy signals, said path specific modules being connected in parallel, and
      a monitor connected to outputs of said first and second signal paths to selectively display the radiography image generated by the first signal path and the fluoroscopy image generated by the second signal path.

9. A method for combining a radiography system and a fluoroscopic system, comprising the steps of:
   providing a radiography radiation generator and receiver for generating a radiography radiation signal from a radiography beam;
   providing a fluoroscopy radiation generator and receiver for generating a fluoroscopy radiation signal from a fluoroscopy beam; and
   processing said radiography radiation signal and said fluoroscopy radiation signal in a single computer, said single computer including common modules which process said radiography radiation signal and which process said fluoroscopy radiation signal, and said single computer including path specific processes which process respectively one of the radiation signal and said fluoroscopy radiation signal, said path specific processes being connected in parallel.

10. A method for combining a radiography system and a fluoroscopic system, comprising the steps of:
providing a radiography radiation generator and receiver for generating a radiography radiation signal from a radiography beam;
providing a fluoroscopy radiation generator and receiver for generating a fluoroscopy radiation signal from a fluoroscopy beam; and
processing said radiography radiation signal in a first computer and processing said fluoroscopy radiation signal in a second computer, said first and second computers including a substantially identical program operating on both computers, said substantially identical program having common modules which process said radiography radiation signal in said first computer and said fluoroscopy radiation signal in said second computer, said program having path specific processes which process respectively one of the radiation signal and said fluoroscopy radiation signal, said path specific processes being connected in parallel.

11. A method for combining a radiography system and a fluoroscopic system, comprising the steps of:
providing a radiography radiation generator for generating a radiography beam;
providing a fluoroscopy radiation generator for generating a fluoroscopy beam;
providing a single radiation receiver for generating a radiography radiation detector signal from the radiography beam and for generating a fluoroscopy radiation detector signal from the fluoroscopy beam; and
processing said radiography radiation detector signal and said fluoroscopy radiation detector signal in a single computer, said single computer including common modules that are shared for processing both said radiography radiation detector signal and said fluoroscopy radiation detector signal, and said single computer having path specific processes which process respectively one of the radiation signal and said fluoroscopy radiation signal, said path specific processes being connected in parallel.

* * * * *